US00PP31936P2

(12) United States Plant Patent
van Geest

(10) Patent No.: US PP31,936 P2
(45) Date of Patent: Jul. 7, 2020

(54) ***FICUS* PLANT NAMED 'ESFIDE162'**

(50) Latin Name: *Ficus deltoidea*
Varietal Denomination: ESFIDE162

(71) Applicant: J. Van Geest Holding B.V., Gravenzande (NL)

(72) Inventor: Jan van Geest, Gravenzande (NL)

(73) Assignee: J. Van Geest Holding B.V., Gravenzande (NL)

( * ) Notice: Subject to any disclaimer, the term of this patent is extended or adjusted under 35 U.S.C. 154(b) by 0 days.

(21) Appl. No.: 16/501,278

(22) Filed: Mar. 16, 2019

(51) Int. Cl.
*A01H 5/12* (2018.01)

(52) U.S. Cl.
USPC ..... Plt./211

(58) Field of Classification Search
USPC ..... Plt./211
See application file for complete search history.

(56) References Cited

PUBLICATIONS

PLUTO Plant Variety Database Nov. 6, 2019.*

* cited by examiner

*Primary Examiner* — Annette H Para
(74) *Attorney, Agent, or Firm* — Samuel R. McCoy, Jr.

(57) ABSTRACT

A new and distinct variety of *Ficus* plant named 'ESFIDE162' which is characterized by the combination of medium-sized broad spatulate foliage with a medium green upper surface which is sparsely dotted greyed-yellow and golden yellow lower surface, and the stability of all characteristics from generation to generation.

3 Drawing Sheets

Latin name of the genus and species: The Latin name of the genus and species of the novel variety disclosed herein is *Ficus deltoidea.*

Variety denomination: The inventive variety of *Ficus* disclosed herein has been given the variety denomination 'ESFIDE162'.

BACKGROUND OF THE INVENTION

Parentage: 'ESFIDE162' originated as a naturally occurring, whole-plant mutation of an unnamed *Ficus deltoidea* plant (not patented). In the summer of 2016, the inventor discovered the mutation at his commercial greenhouse in Gravenzande, The Netherlands, growing amongst a cultivated population of *Ficus deltoidea* plants. The mutation was noted for its medium-sized broad spatulate foliage with a medium green upper surface and golden yellow lower surface and was subsequently isolated for further evaluation in order to confirm the distinctness and stability of the characteristics first observed. Upon confirmation of distinctness and stability, 'ESFIDE162' was selected for commercialization.

Asexual Reproduction: Asexual reproduction of 'ESFIDE162', by way of stem cuttings, was first initiated in the summer of 2016 at a commercial greenhouse in Gravenzande, The Netherlands. Through five subsequent generations, the unique features of this cultivar have proven to be stable and true to type.

SUMMARY OF THE INVENTION

The cultivar 'ESFIDE162' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'ESFIDE162'. These characteristics in combination distinguish 'ESFIDE162' as a new and distinct *Ficus* cultivar:

1. *Ficus* 'ESFIDE162' exhibits inverted deltoid to broad spatulate, medium-sized foliage; and
2. *Ficus* 'ESFIDE162' exhibits foliage with a green adaxial surface, sparsely dotted greyed-orange, and occasionally with black glands at the proximal primary vein axils; and
3. *Ficus* 'ESFIDE162' exhibits foliage with a golden yellow abaxial surface with black glands at the primary vein axils.

BOTANICAL DESCRIPTION OF THE PLANT

Figure 1:
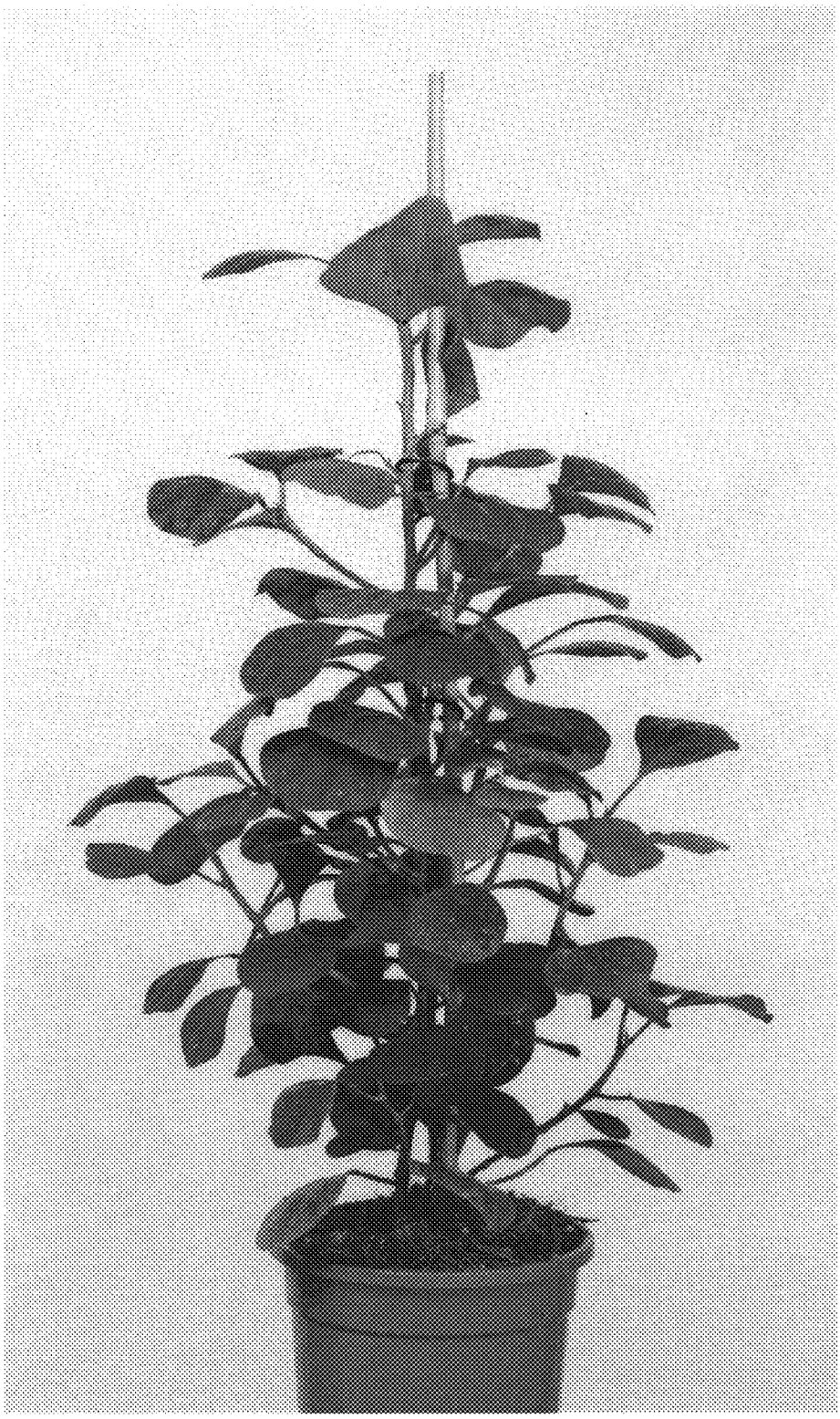
FIG. 1 illustrates, as nearly true as it is reasonably possible to make the same in color photographs of this type, an exemplary plant of 'ESFIDE162' grown in a commercial greenhouse in Gravenzande, The Netherlands. This plant is approximately 20 weeks old, shown planted in a 15 cm container.
Figure 2:
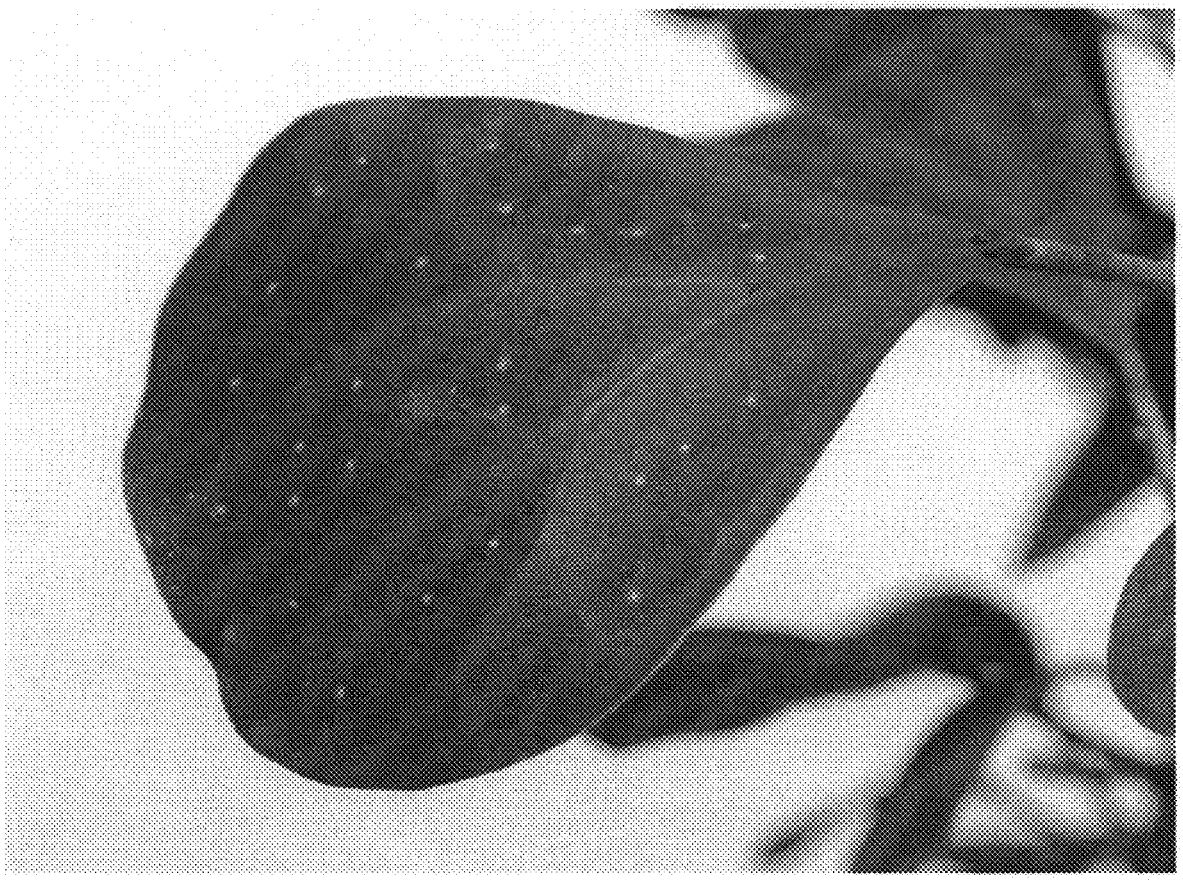
FIG. 2 illustrates, as nearly true as it is reasonably possible to make the same in color photographs of this type, the adaxial surface of the mature foliage of 'ESFIDE162'.
Figure 3:
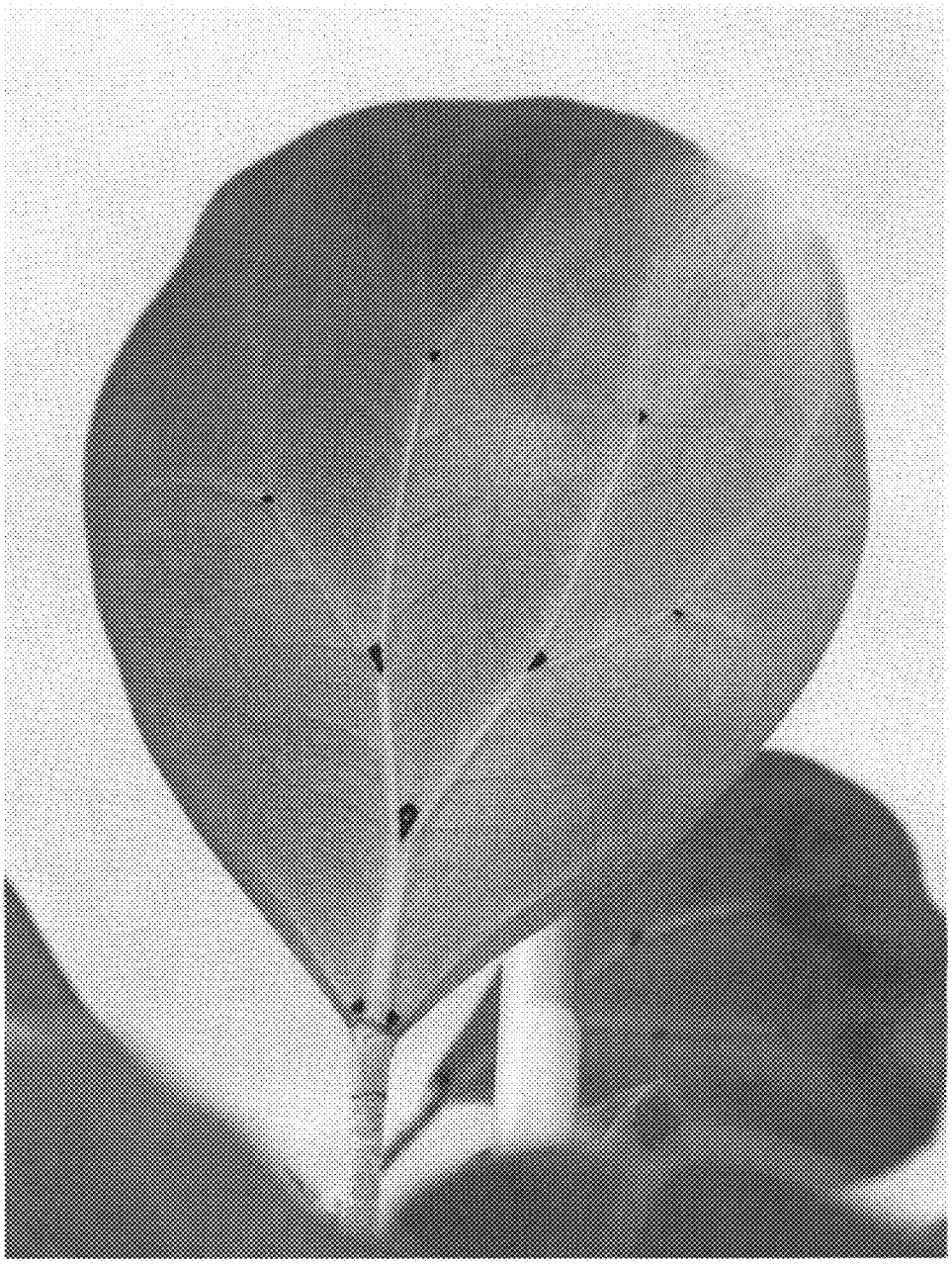
FIG. 3 illustrates, as nearly true as it is reasonably possible to make the same in color photographs of this type, the abaxial surface of the mature foliage of 'ESFIDE162'.

The following observations and measurements were made in February of 2019 and describe a sample set of six 20 week-old 'ESFIDE162' plants grown in 15 cm nursery pots at a greenhouse in Gravenzande, The Netherlands. Plants were produced in a greenhouse with full sun exposure, ebb and flood irrigation tables, no supplemental fertilizer, and no preventative or pest control measures utilized.

Those skilled in the art will appreciate that certain characteristics will vary with older or, conversely, with younger plants. 'ESFIDE162' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart,* The Royal Horticultural Society, London, 2015 (sixth edition).

A botanical description of 'ESFIDE162' and comparisons with the parent plant and most similar commercial variety of *Ficus* are provided below.

Plant description:

*Growth habit*.—Upright.

*Plant profile*.—Ovate.

*Average height*.—55.9 cm from the soil level to the top of the foliar plane.

*Plant spread*.—Average of 39.1 cm.

*Growth rate*.—Moderately fast growing.

*Plant vigor*.—Moderately vigorous.

*Propagation type*.—Stem cuttings.

*Time to produce a rooted cutting*.—Approximately 40 days to produce a rooted cutting at approximately 25 degrees Celsius.

*Time to produce a finished plant*.—Approximately 18 weeks to produce a marketable finished plant in a 17 cm pot.

*Disease resistance*.—Neither resistance nor susceptibility to typical *Ficus deltoidea* pests and diseases has been observed.

*Environmental tolerances*.—Adapt to, at least, USDA Zones 10 through 13 and temperatures as high as 40 degrees Celsius; moderate to high tolerance to rain; moderate tolerance to wind.

Root system:

*General*.—Moderately dense, moderately branched rooting; roots are slightly fibrous.

*Distribution in the soil profile*.—Shallow to moderately deep.

*Diameter of roots*.—0.8 mm on average.

*Texture*.—Smooth; no root hairs.

*Color*.—Greyed-yellow, nearest to RHS 162C.

Stem:

*General branching habit*.—Basally branching main stems; with lateral branching. Stems produce a milky exudate when damaged.

*Main stem*.—Quantity — 2. Attitude — Upright. Aspect — Rounded. Strength — Strong. Color, immature stems — Yellow-green, nearest to RHS 144B. Color, mature stems — Yellow-green, nearest to RHS 146A. Color at internodes — Yellow-green, nearest to RHS 146A. Color, oldest wood — Greyed-brown, nearest to RHS 194A. Texture — Glabrous with small elliptical lenticels with an average length of 0.5 mm and a width of 0.2 mm. Luster — Matte.

*Lateral branches*.—Quantity — 12. Length — 16.2 cm. Diameter — 4.0 cm. Internode length — 3.3 cm. Attitude — At an approximate angle of 55 degrees to the main stems. Aspect — Rounded. Strength — Moderately strong. Texture — Densely covered with a fibrous layer, colored greyed-yellow, nearest to RHS 161D. Luster — Matte. Color, immature stems — Yellow-green, nearest to RHS 144B. Color, mature stems — Yellow-green, nearest to RHS 146A. Color at internodes — Yellow-green, nearest to RHS 146A.

Foliage:

*Arrangement*.—Alternate.

*Division*.—Simple.

*Quantity*.—5 leaves per lateral branch.

*Attitude*.—At an average angle of 60 degrees to the branch.

*Lamina*.—Shape — Inverted deltoid to broad spatulate. Aspect — Slightly convex. Dimensions — 7.5 cm long and 6.6 cm wide. Apex — Truncate to undeeply broad emarginate. Base — Acuminate. Margin — Entire; coarsely undulate and very slightly involute. Texture and luster of the adaxial surface — Smooth, glabrous, and matte. Texture and luster of the abaxial surface — Smooth, glabrous, and matte. Color — Juvenile foliage, adaxial surface — Yellow-green, nearest to RHS 146A, and sparely dotted lighter green nearest to RHS 153D. Juvenile foliage, abaxial surface — Greyed-brown, nearest to RHS 199B, and veined yellow-green, nearest to RHS 145B. Small glands colored greyed-purple to black, nearest to a combination of RHS N186A and 203B, are visible on the proximal vein axils. Mature foliage, adaxial surface — Green, nearest to RHS NN137A, and narrowly margined yellow-green to greyed-green, in between RHS 152D and 161A. Leaves are sparsely dotted greyed-orange, nearest to RHS N163D; dots are approximately 0.5 mm in diameter. Mature foliage, abaxial surface — Yellow-green to greyed-green, in between RHS 152D and 161A. Venation — Pattern — Pinnate. Color, adaxial surface — Green, nearest to RHS NN137B. Small glands colored greyed-purple to black, nearest to a combination of RHS N186A and 203B, are visible on the proximal vein axils. Color, abaxial surface — Yellow-green, nearest to a mixture of RHS 145A and 145B. Small glands colored greyed-purple to black, nearest to a combination of RHS N186A and 203B yet closest to 203B, are visible on the primary vein axils.

*Stipule*.—Not present.

*Petiole*.—Length — 2.6 cm. Diameter — 3.0 cm. Strength — Strong. Texture — Densely covered with a fibrous layer, colored greyed-yellow, nearest to RHS 161D. Luster — Matte. Color, adaxial surface — Yellow-green, nearest to RHS 146A. Color, abaxial surface — Yellow-green, nearest to RHS 146B.

Inflorescence: No flowering has been observed to date.

Comparison with the parent plant: Plants of the new cultivar 'ESFIDE162' differ from the parent, an unnamed *Ficus deltoidea* plant (not patented) in the following characteristics described in Table 1 below.

TABLE 1

| Characteristic | 'ESFIDE162' | The parent |
|---|---|---|
| Foliage abundance. | Less abundant. | More abundant. |
| Foliage size. | Larger than the parent. | Smaller than 'ESFIDE162' |
| Foliage shape. | Inverted deltoid to broad spatulate. | Inverted deltoid to orbicular. |
| General coloration of the mature foliage. | Lighter green. | Darker green. |

Comparison with the closest known comparator: Plants of the new cultivar 'ESFIDE162' differs from the variety, *Ficus* sp. 'ESFIDE161' (Community Plant Variety Rights application number 2016/3129) in the following characteristics described in Table 2 below.

TABLE 2

| Characteristic | 'ESFIDE162' | 'ESFIDE161' |
|---|---|---|
| Abundance of foliage. | Less abundant. | Moreabundant. |
| Foliage size. | Larger than 'ESFIDE161'. | Smaller than 'ESFIDE162'. |
| Foliage shape. | Broader than 'ESFIDE161'. | Narrower than 'ESFIDE162'. |
| Presence of spots on foliage. | Present. | Absent. |
| General coloration of the adaxial foliage surface. | Generally appearing as more toward yellow | Generally appearing as more towards yellow-green. |

That which is claimed is:

1. A new and distinct variety of *Ficus* plant named 'ESFIDE162', substantially as described and illustrated herein.

* * * * *